(12) United States Patent
Kuth et al.

(10) Patent No.: US 6,304,085 B2
(45) Date of Patent: Oct. 16, 2001

(54) AUXILIARY APPARATUS FOR A MAGNETIC RESONANCE TOMOGRAPHY APPARATUS CONTROL UNIT

(75) Inventors: Rainer Kuth, Herzogenaurach; Markus Vester, Nuernberg, both of (DE)

(73) Assignee: Siemens Aktiengesellschaft ( * ) Notice: Subject to any disclaimer, the term of this patent is extended or adjusted under 35 U.S.C. 154(b) by 0 days.

(21) Appl. No.: 09/776,053

(22) Filed: Feb. 2, 2001

(30) Foreign Application Priority Data

Feb. 2, 2000 (GB) .................................................. 10004423

(51) Int. Cl.$^7$ ..................................................... G01V 3/00
(52) U.S. Cl. ............................................. 324/322; 324/318
(58) Field of Search ..................................... 324/322, 318, 324/300, 306, 307, 309, 312, 314

(56) References Cited

U.S. PATENT DOCUMENTS

| | | | |
|---|---|---|---|
| 4,446,431 | 5/1984 | McKay | 324/318 |
| 4,691,163 | 9/1987 | Blass et al. | 324/318 |
| 4,873,486 | 10/1989 | Kuhn et al. | 324/307 |
| 5,250,944 | * 10/1993 | Urbas et al. | 324/322 |
| 5,442,292 | 8/1995 | Kolem et al. | 324/322 |
| 5,483,158 | * 1/1996 | van Heteren et al. | 324/318 |

* cited by examiner

*Primary Examiner*—Louis Arana
(74) *Attorney, Agent, or Firm*—Schiff Hardin & Waite

(57) ABSTRACT

An additional apparatus for a control device for a magnetic resonance tomography apparatus converts an output signal emitted by the control device from an initial frequency into a second frequency. Magnetic resonance signals are excited by the modified output signal. The excited magnetic resonance signals are received. The auxiliary apparatus converts the reception signal back into the initial frequency.

10 Claims, 3 Drawing Sheets

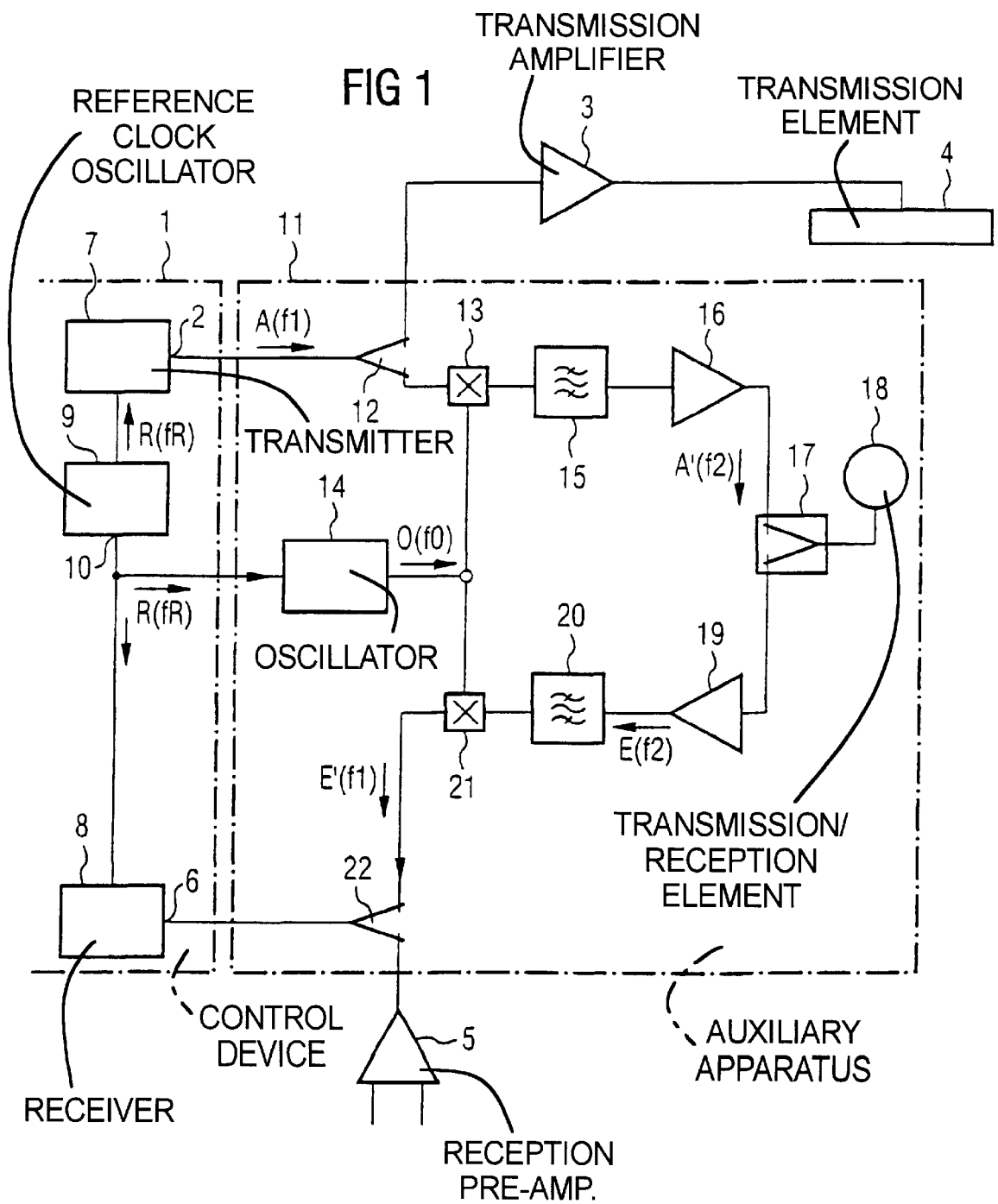

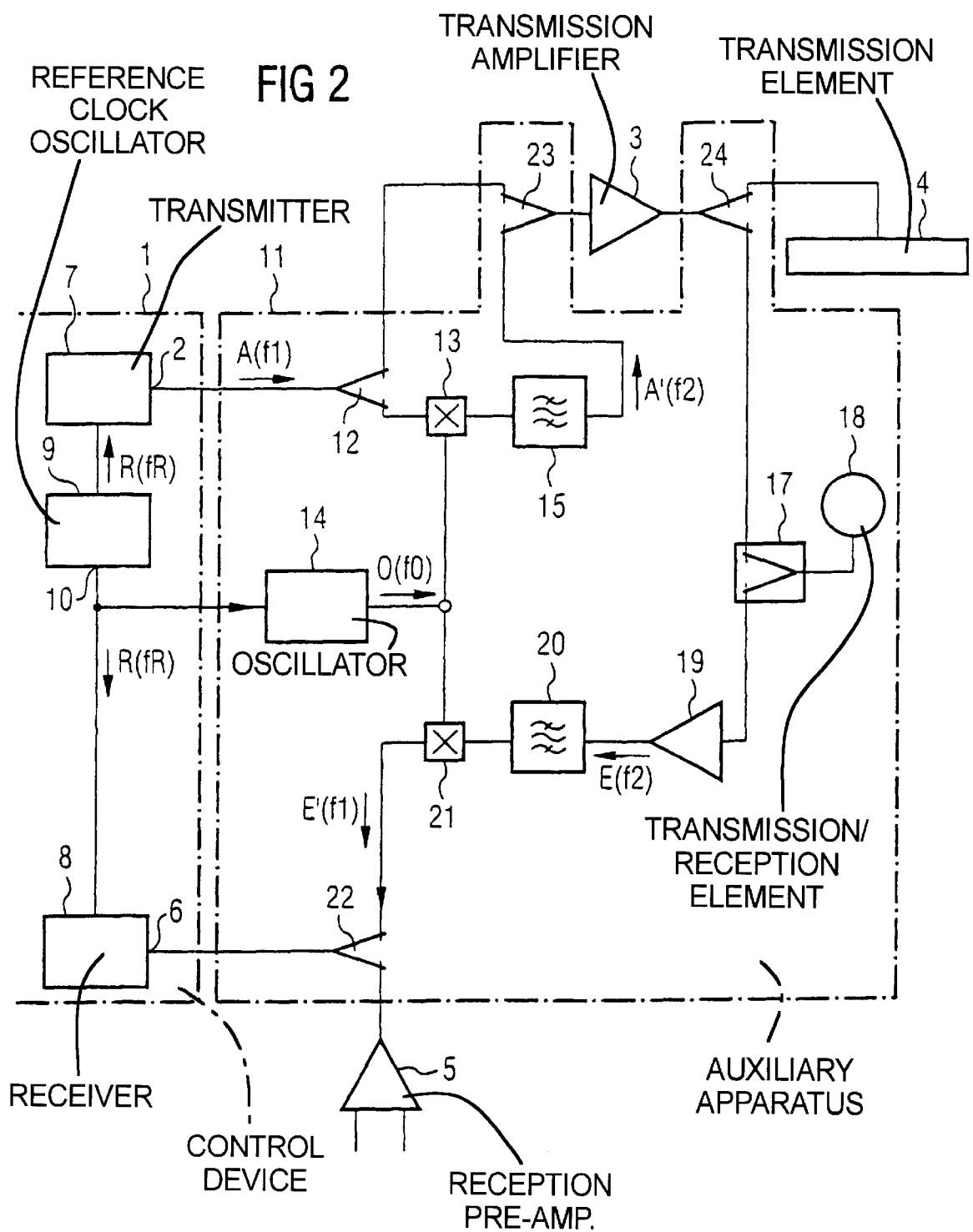

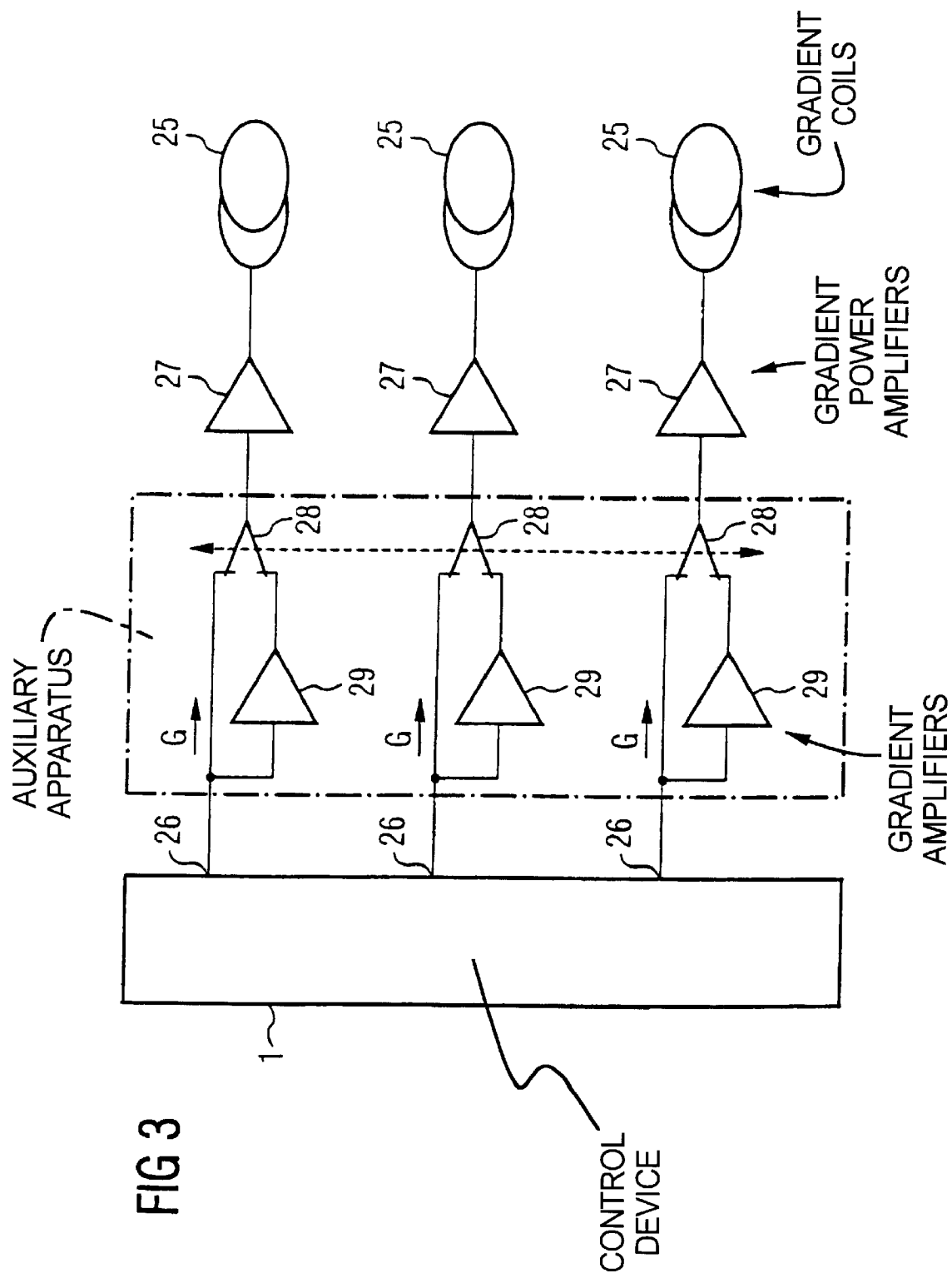

AUXILIARY APPARATUS FOR A MAGNETIC RESONANCE TOMOGRAPHY APPARATUS CONTROL UNIT

BACKGROUND OF THE INVENTION

1. Field of the Invention

The present invention relates to an auxiliary apparatus for a control device for a magnetic resonance tomography apparatus, the control device being of the type which emits an output signal via a transmission output and an Input signal produced by the output signal is fed into the control device via a reception input, and wherein the output signal exhibits an initial frequency and the input signal can be properly processed by the control device only when it exhibits the initial frequency.

2. Description of the Prior Art

Magnetic resonance tomography devices and their control devices are generally known. Normally, the control devices can only emit a prescribed frequency via the transmission output. The Input signal usually can be properly processed only when it (within the bandwidth of a sequence) exhibits this frequency. The frequency normally corresponds to the Larmor frequency of a hydrogen nucleus, which is for example 8.25 MHZ. The bandwidth is ±300 kHz, for example.

Control devices for magnetic resonance tomography systems, wherein the primary frequency is variable, are also known. These control devices, however, are very expensive.

SUMMARY OF THE INVENTION

An object of the present invention is to provide an economic way to operate a magnetic resonance tomography apparatus with at least two frequencies.

This object is achieved in an auxiliary apparatus for a magnetic resonance tomography apparatus control device of the type initially described, wherein the output signal is supplied to the auxiliary apparatus, and the output signal is modified by the auxiliary apparatus such that it has a second frequency that is different from the initial frequency. The auxiliary apparatus supplies the modified output signal to a transmission element as a transmission signal. A reception signal received by a reception element and produced by the transmission signal has the second frequency. The reception signal is supplied to the auxiliary apparatus, and the reception signal is modified by the auxiliary apparatus such that it exhibits the initial frequency. The auxiliary apparatus supplies the modified reception signal to the reception input as an input signal.

The magnetic resonance tomography apparatus and the control device can remain unmodified as a result of the invention. The conversion to the second frequency and back occurs in the auxiliary apparatus. Another frequency other than the actual measuring frequency is generated separately from the control device. It is not necessary to adapt the system control, the image calculation software or the other user software.

The second frequency can be prescribed or can be modifiable in steps or continuously. Normally, the second frequency is fixed, or is variable in relatively large steps of 1 MHZ, for example.

The frequency transfer from the primary frequency to the second frequency and back is particularly simple when the auxiliary apparatus has an auxiliary oscillator, which emits an auxiliary oscillator signal, which exhibits an auxiliary oscillator frequency. The auxiliary oscillator signal and the output signal can be supplied to an output signal frequency mixer, which emits the modified output signal, and the auxiliary oscillator signal and the reception signal can be supplied to a reception signal frequency mixer, which emits the modified reception signal.

An output signal filter can follow the output signal frequency mixer, or a reception signal filter can precede the reception signal frequency mixer, so that frequencies that could cause a phantom signal are filtered out.

The auxiliary oscillator frequency can be generated and stabilized in a simple way when the control device, via a reference output, can emit a reference signal exhibiting a reference frequency, and the reference signal can be supplied to the auxiliary oscillator. The auxiliary oscillator derives the auxiliary oscillator frequency from the reference frequency.

The transmission signal is supplied to the transmission element via a transmission amplifier. The transmission amplifier can be optionally arranged in the auxiliary apparatus or can be allocated to the magnetic resonance tomography apparatus.

A particularly simple and compact structure of the unit formed by the auxiliary apparatus and the transmission/reception element is achieved in an embodiment wherein the transmission element and the reception element are combined to form a common transmission/reception element and wherein the auxiliary apparatus is arranged at the common transmission/reception element.

A gradient signal can be emitted by the control device via at least one gradient output. The gradient signal can be supplied to the auxiliary apparatus and when the auxiliary apparatus can amplify the gradient signal by an amplification factor. The amplification factor is equal to the ratio of initial frequency to second frequency, so that the same allocation of location to transmission/reception frequency results for a nucleus having a different gyromagnetic ratio as would occur without the auxiliary apparatus for the basic nucleus (primarily hydrogen).

The auxiliary apparatus can be connected to the control devices via switches, which allows the auxiliary apparatus to be connected to the control device in a fast and simple manner. The switches can be operated together, allowing the auxiliary apparatus to be particularly simply switched on.

DESCRIPTION OF THE DRAWINGS

FIG. 1 shows a high-frequency stage of a magnetic resonance tomography apparatus in accordance with the invention FIG. 2 shows a further version of the high-frequency stage of FIG. 1.

FIG. 3 shows a gradient field control arrangement of a magnetic resonance tomography apparatus in accordance with the invention.

DESCRIPTION OF THE PREFERRED EMBODIMENTS

As shown in FIG. 1, a control device 1 for a magnetic resonance tomography apparatus has a transmission output 2. An output signal A can be emitted via the transmission output 2. The output signal A has an initial frequency f1. The initial frequency f1 corresponds to the Larmor frequency of hydrogen for a specific magnetic field of the magnetic resonance tomography apparatus. The initial frequency f1 is 8 MHZ, for example.

The output signal A is supplied to a transmission amplifier 3 when the magnetic resonance tomography apparatus is normally operated. The transmission amplifier 3 is a power amplifier, which is tuned to the initial frequency f1. The transmission amplifier 3 supplies the amplified output signal A to a transmission element 4. An examination subject (not shown) is thus excited to emit magnetic resonance signals, which are received by a reception element (not shown). The received signal is fed into the control device 1 via a pre-amplifier 5 and a reception input 6, and is processed therein.

As a result of the excitation of the examination subject at the initial frequency f1, the input signal also exhibits the initial frequency f1. The control device 1 can properly process the input signal only when it exhibits the initial frequency f1. A proper representation of the examination subject results only under these conditions.

A transmitter 7 generates the output signal A within the control device 1; the reception signal E within the control device 1 is processed in a receiver 8. The control device 1 also has a reference clock oscillator 9, so that the transmitter 7 and the receiver 8 exhibit exactly the initial frequency f1. The reference clock oscillator 9 emits a reference signal R at a reference frequency fR. The reference frequency fR is 10 MHZ, for example. The reference signal R is supplied to the transmitter 7 and to the receiver 8 and can be tapped at a reference output 10.

For specific examinations such as lung examinations with helium, it would be advantageous for the control device 1 not to be operated at the initial frequency f1, but at a second frequency f2. In order to enable such operation, an auxiliary apparatus 11 is provided, which can be detachably connected to the control device 1.

As shown in FIG. 1, the output signal A can be supplied to the auxiliary apparatus 11 via a switch 12. Within the auxiliary apparatus 11, the output signal A is supplied to an output signal frequency mixer 13. An auxiliary oscillator signal O emitted by an auxiliary oscillator 14 is also supplied to the frequency mixer 13. The auxiliary oscillator signal O has an auxiliary oscillator frequency fO. The reference signal R is supplied to the auxiliary oscillator 14. Therefore, the auxiliary oscillator 14 can derive the auxiliary oscillator frequency fO from the reference frequency fR. The auxiliary oscillator frequency fO is selected such that it is either equal to the sum or to the difference of the initial frequency f1 and the second frequency f2. The output signal frequency mixer 13 therefore emits a modified output signal A'.

In addition to its actual set frequency, i.e., the second frequency f2, the modified output signal A' also has a signal portion with another frequency component. Therefore, the output signal frequency mixer 13 is followed by an output signal filter 15, which filters out all signal portions exhibiting a frequency other than the second frequency f2. The filtered output signal A' therefore only exhibits the second frequency f2.

The output signal filter 15 supplies the modified output signal A' via a transmission amplifier 16 and a changeover switch 17 as a transmission signal to an element 18. The element 18 is fashioned as a common transmission/reception element. Therefore, it is able to transmit magnetic resonance signals and to receive magnetic resonance signals as well.

As can be seen from FIG. 1, the transmission amplifier 16—in contrast to the transmission amplifier 3—is allocated to the auxiliary apparatus 11. A separate transmission amplifier 16 is used, which can be tuned to the second frequency f2.

After the modified output signal A' has been transmitted, the changeover switch 17 is operated and the element 18 receives a reception signal E. The reception signal E is produced by the transmission signal (or by the modified output signal) A' and therefore exhibits the second frequency f2 as well. It is supplied to the auxiliary apparatus 11.

Within the auxiliary apparatus 11, the reception signal E is initially supplied to a preamplifier 19 and subsequently to a reception signal filter 20. The reception signal filter 20 filters out all signal components of the reception signal E which are different from the second frequency f2. The reception signal filter 20 precedes a reception signal frequency mixer 21. The (filtered) reception signal E and the auxiliary oscillator signal O are supplied to the reception signal frequency mixer 21. The reception signal frequency mixer 21 emits a modified reception signal E' at its output. The reception signal E', in turn, exhibits the initial frequency f1. The auxiliary apparatus 11 supplies this signal E' via a switch 22 to the reception input 6. It can be properly evaluated by the receiver 8.

The embodiment according to FIG. 2 generally corresponds to the embodiment of FIG. 1. The same elements therefore are provided with the same reference numbers. In contrast to FIG. 1, the transmission amplifier 3 of the magnetic resonance tomography apparatus is fashioned as a broadband power amplifier. Therefore, it can amplify a signal at the initial frequency f1 as well as a signal at the second frequency f2. In this case, it is possible to optionally supply the unmodified output signal A or the modified output signal A' via a switch 23 to the transmission amplifier 3. Subsequently, the output signal of the transmission amplifier 3 is optionally supplied via a further switch 24 to the transmission element 4 or to the changeover switch 17. In the embodiment according to FIG. 2, the transmission amplifier 3 therefore is allocated to the magnetic resonance tomography apparatus.

The auxiliary apparatus 11 can be integrated with the element 18. This is particularly advantageous when the element 18 is as a local coil for transmitting excitation signals and for receiving the resulting magnetic resonance signals. In this case, a transfer to the desired second frequency f2 and back to the initial frequency f1 automatically results when the local coil 18 is connected to the control device 1.

As shown in FIG. 3, the magnetic resonance tomography apparatus has gradient coils 25. The gradient coils 25 generate a gradient magnetic field, which is superimposed on a constant magnetic field. The gradient magnetic field is scaled with a scaling factor, which depends on the core to be measured and therefore on the second frequency f2. Preferably, not only the signal frequency is transferred from the initial frequency f1 to the second frequency f2, but also the gradient field is correspondingly adapted.

The gradient coils 25 generate the gradient field as a result of gradient signals G, which are supplied by the control device 1 via gradient outputs 26 and which are supplied to the gradient coils 25 via gradient power amplifiers 27. As shown in FIG. 3, switches via which the gradient outputs 26 are optionally directly supplied to the gradient power amplifiers 27, or via gradient amplifiers 29, are arranged preceding the gradient power amplifiers 27. The gradient amplifier 29 and the switches 28 are a part of the auxiliary apparatus 11. The gradient amplifiers 29 amplify the gradient signals with an amplification factor. The amplification factor is equal to the ratio of the respective gyromagnetic constants of the basic core to the core to be measured, and therefore is equal to the ratio of initial frequency f1 to second frequency f2 given an unmodified basic magnetic field.

The switches 12, 22, 23, 24 and 28 shown in FIG. 1 to 3 are preferably rigidly coupled to one another. Therefore, they can be operated together.

Using the auxiliary apparatus 11, a frequency other than the actual measuring frequency is produced separately from the control device. Thus, no modification of the existing components nor an adaptation of the system control, the image calculation software, or the application software are needed. The invention therefore produces considerable cost savings compared to known control devices having a variable initial frequency f1.

Although modifications and changes may be suggested by those skilled in the art, it is the intention of the inventors to embody within the patent warranted hereon all changes and modifications as reasonably and properly come within the scope of their contribution to the art.

We claim as our invention:

1. In a magnetic resonance tomography apparatus having a control device which emits an output signal at a control device output at an initial frequency, said output signal resulting in an input signal, at said initial frequency, being produced outside of said control unit, said control device having a control device input to which said input signal is supplied, said input signal being properly processed by said control device only if said input signal is at said initial frequency, the improvement of an auxiliary apparatus for use with said control device, comprising:

an auxiliary apparatus input, adapted for connection to said control device output, and supplied with said output signal;

a first signal modifier connected to said auxiliary apparatus input for modifying said output signal to produce a modified output signal at a second frequency, different from said initial frequency;

a transmission element connected to said first signal modifier for transmitting said modified output signal as a transmission signal;

a reception element for receiving a reception signal, at said second frequency, produced by said transmission signal;

a second signal modifier connected to said reception element and supplied with said reception signal for modifying said reception signal to produce a modified reception signal at said first frequency; and an auxiliary apparatus output connected to said second signal modifier, and adapted for connection to said control device input, for supplying said modified reception signal to said control device input as said input signal.

2. An auxiliary apparatus as claimed in claim 1 wherein said first signal modifier and said second signal modifier comprise:

an oscillator which emits an oscillator signal at an oscillator frequency;

a first signal mixer supplied with said oscillator signal and with said output signal for producing said modified output signal by mixing said output signal with said oscillator signal; and a second signal mixer supplied with said oscillator signal and with said reception signal for producing said modified reception signal by mixing said oscillatory signal and said reception signal.

3. An auxiliary apparatus as claimed in claim 2 further comprising a filter connected between said first signal mixer and said transmission element for filtering any frequencies out of said modified output signal which are different from said second frequency.

4. An auxiliary apparatus as claimed in claim 2 comprising a filter connected between said reception element and said second signal mixer for filtering any frequencies out of said reception signal which are different from said second frequency.

5. An auxiliary apparatus as claimed in claim 2 wherein said control device has a reference signal output at which a reference signal is emitted at a reference frequency, and wherein said auxiliary apparatus comprises a reference signal input connected to said oscillator, and adapted for connection to said reference signal output for supplying said reference signal to said oscillator, and wherein said oscillator derives said oscillator frequency of said oscillator signal from the reference frequency of the reference signal.

6. An auxiliary apparatus as claimed in claim 1 further comprising a transmission amplifier connected between said first signal modifier and said transmission element.

7. An auxiliary apparatus as claimed in claim 1 wherein said transmission element and said reception element comprise a combined transmission/reception element, and a switch connected between said transmission/reception element and each of said first signal modifier and said second signal modifier for connecting said first signal modifier and said second signal modifier to said transmission/reception element one at a time.

8. An auxiliary apparatus as claimed in claim 1 wherein said control device emits a gradient signal as said output signal, and wherein said auxiliary apparatus includes a gradient amplifier for amplifying said gradient signal with an amplification factor which is equal to a ratio of said initial frequency to said second frequency.

9. An auxiliary apparatus as claimed in claim 1 comprising at least a first switch for selectively connecting said auxiliary apparatus input to said first signal modifier and a second switch for selectively connecting said second signal modifier to said auxiliary apparatus output.

10. An auxiliary apparatus as claimed in claim 9 wherein said first and second switches are operated in combination.

* * * * *